United States Patent [19]

Hashimoto et al.

[11] Patent Number: 4,465,878
[45] Date of Patent: Aug. 14, 1984

[54] PROCESS FOR PRODUCING 4',4-DIHYDROXYDIPHENYL

[75] Inventors: Takeshi Hashimoto; Terumasa Akashi; Koji Nishihara, all of Wakayama, Japan

[73] Assignee: Sugai Chemical Industry Co., Ltd., Wakayama, Japan

[21] Appl. No.: 400,421

[22] Filed: Jul. 21, 1982

[30] Foreign Application Priority Data

Jul. 23, 1981 [JP] Japan .................................. 56-114469

[51] Int. Cl.$^3$ ...................... C07C 37/04; C07C 39/12
[52] U.S. Cl. .................................... 568/730; 568/738; 568/769; 568/795
[58] Field of Search ................ 568/769, 730, 738, 795

[56] References Cited

U.S. PATENT DOCUMENTS

| 2,368,361 | 1/1945 | Jenkins | 568/730 |
| 4,243,822 | 1/1981 | Demler et al. | 568/730 |
| 4,324,926 | 4/1982 | Demler et al. | 568/730 |

Primary Examiner—Werren B. Lone
Attorney, Agent, or Firm—Armstrong, Nikaido, Marmelstein & Kubovcik

[57] ABSTRACT

A process for producing 4,4'-dihydroxydiphenyl which comprises subjecting to alkali fusion 1 mol of 4,4'-diphenyldisulfonic acid and/or potassium 4,4'-diphenyldisulfonate together with 4 to 10 mol of potassium hydroxide and 0.1 to 2 mol of potassium sulfate. Alternatively, the process may comprise subjecting to alkali fusion 4,4'-diphenyldisulfonic acid in the presence of potassium hydroxide, controlling to 20 to 25% the potassium hydroxide concentration in the reaction mixture, and separating dipotassium salt of 4,4'-dihydroxydiphenyl.

16 Claims, No Drawings

PROCESS FOR PRODUCING 4',4-DIHYDROXYDIPHENYL

BACKGROUND OF THE INVENTION

The present invention relates to a process for producing 4,4'-dihydroxydiphenyl and, more particularly, a process for obtaining high purity 4,4'-dihydroxydiphenyl in a high yield by the alkali fusion of 4,4'-diphenyldisulfonic acid with potassium hydroxide.

Recently, the range of use of heat-resistant synthetic polyester resins as engineering plastics has been increasing. For realizing functional polymer characteristics of the engineering plastics, it is indispensable requisites that high purity monomers be used as the starting material and contamination of the polymer with unreacted matters, isomers or inorganic matters be avoided as far as possible.

4,4'-dihydroxydiphenyl (hereinafter referred to as DHDP) is an important monomer used as a starting material of the engineering plastics.

Generally, DHDP is produced by the alkali fusion of 4,4'-diphenyldisulfonic acid (hereinafter referred to as DPDS). For facilitating the stirring of the reaction system to accelerate the hydroxylation reaction, the following processes have been employed in general: (1) a process wherein a large excess amount of sodium hydroxide is used, (2) a process wherein benzenesulfonic acid is used as a solvent in the alkali fusion reaction, (3) a process wherein the reaction temperature is lowered and potassium hydroxide is used for inhibiting the side reactions to increase the yield, (4) a process wherein potassium hydroxide and sodium hydroxide are used together and (5) a process wherein the use of a large excess amount of an alkali is avoided.

As process (1), there may be mentioned, for example, a process wherein 14-40 mol of sodium hydroxide is used (Japanese Patent Laid-Open No. 112844/1979). In this process, however, complicated steps are required for recovering excessive caustic soda and concentrating the same after completion of the reaction and yet the sodium hydroxide recovery is poor. This process is, therefore, economically disadvantageous.

Namely, after completion of the reaction, the reaction mixture comprises an excessive alkali containing the intended alkali metal salt of DHDP and inorganic salts such as an alkali metal sulfite formed in a rate of nearly 2 mols per mol of the disulfonic acid.

Thus, process (1) inevitably has problems of (a) the recovery of the excessive alkali in a reusable state and (b) the removal of inorganic salts which contaminate intended DHDP. Some processes for solving these problems have been proposed.

For example, for solving problem (a), there has been proposed a process wherein only the excessive alkali is recovered with water and reused (Japanese Patent Laid-Open No. 112844/1979). However, in this process, it is difficult to separate inorganic salts from the alkali metal salt of DHDP without causing a loss of the latter.

For solving problem (b), there has been proposed, for example, a process wherein the alkali metal salt of DHDP is extracted with an alcohol having up to 5 carbon atoms (Japanese Patent Laid-Open No. 108031/1974). This process has a defect that the alkali cannot be recovered or reused, since the excessive alkali is also extracted.

As process (2), there may be mentioned a process of U.S. Pat. No. 2,368,361 which has an advantage that phenol is also obtained by the alkali fusion of benzenesulfonic acid used as the solvent. However, this process is now unattractive, since a more advantageous process for producing phenol alone has been established already.

In processes (3) and (4), an alkali is used generally in a large excess amount in order to facilitate the stirring by reducing the viscosity of the reaction mixture or because of the restriction in the procedure to be effected after completion of the reaction.

Therefore, the processes (3) and (4) have disadvantages that the alkali recovery rate is poor and the effective separation of inorganic salts from DHDP is difficult as in process (1).

As for process (5), there may be mentioned, for example, a process of Japanese Patent Laid-Open No. 52142/1976 which comprises adding sodium hydroxide flakes to powdery sodium 4,4'-diphenyldisulfonate while the reaction system is kept always in a powdery state. In this process, it is difficult from the viewpoint of the operation to keep the reaction system always in a powdery state, since water is formed by the reaction. Another disadvantage of this process is its poor yield.

SUMMARY OF THE INVENTION

A first object of the present invention is to provide a process for producing DHDP suitable for use as a monomer used as a starting material of heat-resistant synthetic polyester resins.

A second object of the present invention is to provide a process for producing high quality DHDP in a high yield.

A third object of the present invention is to provide a process for producing DHDP wherein an alkali hydroxide is used in an amount far smaller than that used in conventional processes.

A fourth object of the present invention is to provide a process for producing DHDP wherein no by-product is formed at all.

A fifth object of the present invention is to provide a process for producing DHDP wherein dipotassium salt of DHDP, inorganic salts and excessive potassium hydroxide contained in the reaction mixture after the alkali fusion are isolated separately from one another to prevent the intended product from being contaminated with them.

A sixth object of the present invention is to provide an economically advantageous process for producing DHDP on an industrial scale.

These objects of the present invention can be attained by a process for producing DHDP by fusing DPDS or its salt in the presence of potassium hydroxide wherein the alkali fusion is carried out by using 4-10 mol of potassium hydroxide and 0.1-2 mol of potassium sulfate per mol of DPDS and/or potassium salt thereof.

The objects of the present invention can be attained also by a process wherein water is added to the reaction mixture after the alkali fusion to control the potassium hydroxide concentration to 20-25%, precipitating DHDP in the form of crystals of its dipotassium salt, the crystals are filtered out, the filtrate is concentrated to a potassium hydroxide concentration of 40-60%, potassium sulfite thus precipitated is separated from the aqueous potassium hydroxide solution, the crystals of dipotassium salt of DHDP are dissolved in water and neutralized with an acid, crude crystals or DHDP are separated, and after dried, dissolved in at least one solvent selected from the group consisting of aliphatic alcohols having 3-8 carbon atoms and aliphatic carboxylic acid esters having 3-8 carbon atoms in total in the presence of active carbon, the active carbon is filtered and the solvent is removed to obtain DHDP.

DESCRIPTION OF THE PREFERRED EMBODIMENTS

In the process of the present invention for producing DHDP, DPDS and/or its potassium salt are/is subjected to the alkali fusion with potassium hydroxide in the presence of potassium sulfate.

The amount of potassium hydroxide is 4-10 mol per mol of DPDS and/or its potassium salt. The amount of potassium sulfate is generally 0.1-2 mol, preferably 0.2-1.0 mol, per mol of DPDS and/or its potassium salt.

The potassium salt of DPDS may be any of monopotassium salt, dipotassium salt and mixture of them.

If potassium hydroxide is used alone, it is necessitated in a large excess amount relative to DPDS as in conventional processes. In addition, in such a case, p-phenylphenol is by-produced in an increased amount and the decomposition reaction also occurs to reduce the yield unfavorably.

If the amount of potassium hydroxide is less than 4 mol, a part of 4,4'-diphenyldisulfonic acid remains unreacted even if the reaction is carried out in the presence of an adequate amount of potassium sulfate and it becomes difficult to obtain high quality DHDP.

If the amount of potassium hydroxide is, on the other hand, more than 10 mol, excessive potassium hydroxide remains after completion of the reaction economically disadvantageously.

If the amount of potassium sulfate is less than 0.1 mol, DHDP yield is poor even if the reaction is carried out in the presence of an adequate amount of potassium hydroxide. This is industrially disadvantageous.

Even if the amount of potassium sulfate is more than 2 mol, yield of DHDP is no more increased.

The alkali fusion conditions in the present invention are not particularly limited but those in conventional processes wherein potassium hydroxide is used may be employed.

For example, the fusion temperature is generally 280°-330° C. and fusion time is 1-5 h.

In the process of the present invention, the amount of potassium hydroxide is reduced to 4-10 mol per mol of DPDS, since it is used in combination with potassium sulfate.

Therefore, in the process of the present invention, the treatment for recovering excessive potassium hydroxide may be omitted after the alkali fusion reaction or, alternatively, the treatment may be effected to recover excessive potassium hydroxide.

In case potassium hydroxide is not recovered, the reaction mixture is cooled to room temperature in an ordinary manner after completion of the alkali fusion reaction, then, the reaction mixture is dissolved in water, an insoluble matter is filtered out, the filtrate is neutralized with an acid to precipitate DHDP crystals and the crystals thus formed are filtered, washed with water and dried.

In case excessive potassium hydroxide is recovered, the reaction mixture is treated as described below after the alkali fusion with potassium hydroxide according to the present invention.

The method of recovering potassium hydroxide after completion of the alkali fusion according to the present invention can be applied not only to the alkali fusion reaction mixture obtained by using the combination of potassium sulfate and potassium hydroxide but also to a reaction mixture obtained by the alkali fusion of DPDS with only potassium hydroxide used in a large excess amount according to the conventional processes.

When potassium hydroxide is recovered, potassium sulfate contained in the mixture is also recovered and it may be used again in the alkali fusion reaction.

The method of recovering potassium hydroxide according to the present invention will be illustrated with reference to a case wherein DPDS is subjected to the alkali fusion with only potassium hydroxide used in a large excess amount as in the conventional processes.

According to the present invention, DPDS is subjected to the alkali fusion with a large excess amount of potassium hydroxide. Water is added to the reaction mixture to control potassium hydroxide concentration to 20-25%. Dipotassium salt of DHDP (A) thus precipitated is separated. On the other hand, the filtrate (B) is concentrated to a potassium hydroxide concentration of 40-60% and the thus precipitated potassium sulfite crystals are separated out of the aqueous potassium hydroxide solution.

Dipotassium salt of DHDP (A) obtained above is dissolved in water and the solution is neutralized with an acid. Crude crystals of 4,4'-dihydroxydiphenyl thus formed are separated, dried to obtain a water content in the crude crystals less than 1%, and dissolved in at least one solvent selected from the group consisting of aliphatic alcohols having 3-8 carbon atoms and aliphatic carboxylic acid esters having 3-8 carbon atoms in total in the presence of active carbon. The active carbon is filtered out and then the solvent is removed to obtain purified DHDP.

Crystals of potassium sulfite formed by concentrating the above-mentioned filtrate (B) to a potassium hydroxide concentration of 40-60% are separated from the aqueous potassium hydroxide solution.

In the process of the present invention, water must be added to the reaction mixture after completion of the alkali fusion to control potassium hydroxide concentration to 20-25%.

If the potassium hydroxide concentration is below 20%, crystals of dipotassium salt of DHDP (A) are not formed sufficiently. On the other hand, if the potassium hydroxide concentration is above 25%, potassium sulfite crystallizes out in addition to dipotassium salt of DHDP (A) unfavorably.

The reaction conditions of the alkali fusion with potassium hydroxide, i.e. mol number of potassium hydroxide, fusion temperature and time, are not particularly limited. For example, the alkali fusion may be carried out using 10-15 mol of potassium hydroxide at the same reaction temperature for the same reaction period of time as those mentioned above as in the conventional processes. Any of the reactions mixture obtained by the alkali fusion according to the conventional processes can be treated by the process of the present invention.

After controlling the potassium hydroxide concentration to 20-25%, the reaction mixture is generally cooled to room temperature to precipitate DHDP as crystals of its dipotassium salt (A) and the crystals are separated out of the filtrate (B).

The obtained dipotassium salt of DHDP (A) may be used, if necessary, for various purposes. It may be converted into the free dihydroxyl compound by dissolving the same in water, generally removing an insoluble matter, neutralizing the solution with, for example, sulfuric acid and filtering the resulting crystals to obtain DHDP.

DHDP generally containing inorganic ashes is dried to show a water content less than 1% and then treated by dissolving the same in a solvent, adding active carbon to the solution, filtering an insoluble matter and active carbon and removing the solvent from the filtrate by, for example, distillation to obtain purified DHDP having a reduced ash content.

When the water content in DHDP exceeds 1%, the purification attainment by active carbon cannot be sufficiently high.

The solvent used for the purification is at least one compound selected from the group consisting of aliphatic alcohols having 3–8 carbon atoms and aliphatic carboxylic acid esters having 3–8 carbon atoms in total. They include, for example, n-butanol, n-propanol, isopropanol, octanol, ethyl acetate and mixtures of them.

The above-mentioned filtrate (B) is concentrated to a potassium hydroxide concentration of 40–60% to form potassium sulfite crystals.

If the potassium hydroxide concentration is less than 40%, the precipitation of potassium sulfite crystals is insufficient. If it is higher than 60%, on the other hand, the crystallization of potassium sulfite and the separation of recovered potassium hydroxide become difficult unfavorably.

The potassium sulfite crystals are filtered out to obtain an aqueous potassium hydroxide solution which can be used for the alkali fusion repeatedly 10 times or more after the treatment with active carbon.

In the process of the present invention, potassium hydroxide is used in an amount of 4–10 mol, namely, in a small excess amount (1–2.5 times as much as a stoichiometric amount), since it is used in combination with potassium sulfate. As compared with the conventional processes wherein an alkali hydroxide is used in an amount 3.5–10 times as much as a stoichiometric amount, the amount of the alkali hydroxide can be reduced remarkably.

Consequently, the recovery or the concentration of the alkali after completion of the reaction may be omitted without exerting significant influences on the production cost of DHDP.

In the process of the present invention wherein a solvent such as benzenesulfonic acid is not used, by-products are not formed at all by the alkali fusion. Further, the alkali fusion reaction is accelerated by the use of potassium sulfate and, therefore, DHDP can be produced in a high yield. Thus, the process of the present invention is suitable for the production of DHDP which is a monomer used for the production of engineering plastics on an industrial scale.

According to the present invention, dipotassium salt of DHDP, potassium sulfite and excessive potassium hydroxide contained in the reaction mixture after the alkali fusion can be removed separately from one another to prevent the intended product from being contaminated with them as far as possible.

Thus, DHDP obtained by the neutralization of dipotassium salt of DHDP with an acid followed by the treatment with active carbon in a solvent has a high purity and an inorganic salt content of as low as up to 100 ppm, while it has been difficult to efficiently remove the inorganic salts by conventional techniques. DHDP obtained by the process of the present invention is, therefore, suitable for use as a starting material of engineering plastics.

The aqueous potassium hydroxide solution separated out has a potassium hydroxide concentration in the range of 40–60% and, therefore, it may be used repeatedly after the treatment with active carbon.

Potassium sulfite separated out can be used for the neutralization of, for example, diphenyldisulfonic acid.

It is apparent from the above description that the process of the present invention is an economically advantageous process for the production of DHDP on an industrial scale.

DPDS used as the starting material in the process of the present invention may be produced by any of various known processes and DPDS produced by these processes may be used as it is.

It is particularly preferred, however, to use DPDS produced by the following processes as the starting material of the present invention, since high purity DPDS is eagerly demanded for the production of heat-resistant engineering plastics.

One of the processes comprises adding a sulfonating agent such as sulfuric acid (e.g. 98% sulfuric acid) or chlorosulfonic acid to molten diphenyl at 130°–145° C., cooling the reaction mixture when the crystallization of DPDS begins in this temperature range to 115°–127° C. and maintaining the reaction mixture in this temperature range for 2–4 h to complete the disulfonation reaction and to obtain DPDS.

Another process comprises adding a sulfonating agent to diphenyl under, for example, the above-mentioned conditions, adding water to the reaction mixture to control the sulfuric acid concentration to 45–55%, adding at least a stoichiometric amount of a potassium salt of an inorganic acid such as potassium sulfate, potassium sulfite or potassium carbonate and/or potassium hydroxide to the mixture while the mixture is heated to 140° C. and leaving them to stand for 1–5 h to obtain monopotassium salt of DPDS.

The following examples will further illustrate the process of the present invention, which by no means limit the invention.

EXAMPLE 1

98 g (0.25 mol) of dipotassium 4,4'-diphenyldisulfonate, 117 g (2.0 mol) of potassium hydroxide and 45 g (0.25 mol) of potassium sulfate were charged in a 1 l iron reaction vessel of a roll mill type. The temperature was elevated under stirring and the reaction was carried out at 320°–330° C. for 3 h. After completion of the reaction, the reaction mixture was cooled to room temperature and 500 ml of water was added to the mixture to dissolve the reaction product therein. An insoluble matter was filtered out and diluted sulfuric acid such as 50% sulfuric acid was added to the filtrate to form crystals. After the filtration, washing with hot water and drying, 43 g of 4,4'-dihydroxydiphenyl was obtained in the form of white crystals. Yield: 92%.

COMPARATIVE EXAMPLE

The reaction was carried out at 320°–330° C. for 5 h under the same conditions as in Example 1 except that potassium sulfate was not used. The reaction product was treated in the same manner as in Example 1 to obtain 31 g of 4,4'-dihydroxydiphenyl in the form of white crystals. Yield: 67%.

EXAMPLE 2

98 g (0.2 mol) of dipotassium 4,4'-diphenyldisulfonate, 66 g (1.13 mol) of potassium hydroxide and 26 g (0.15 mol) of potassium sulfate were reacted under the same conditions as in Example 1. After completion of the reaction, the reaction product was treated in the same manner as in Example 1 to obtain 40.5 g of 4,4'-dihydroxydiphenyl in the form of white crystals. Yield: 87%.

EXAMPLE 3

98 g (0.2 mol) of dipotassium 4,4'-diphenyldisulfonate, 102 g (1.75 mol) of potassium hydroxide and 12 g (0.07 mol) of potassium sulfate were reacted under the same conditions as in Example 1. After the same treatment as above, 41 g of 4,4'-dihydroxydiphenyl was obtained. Yield: 88%.

EXAMPLE 4

101 g (0.25 mol) of monopotassium 4,4'-diphenyldisulfonate (87% purity, 5% sulfuric acid content and 8% water content), 124 g (2.12 mol) of potassium hydroxide and 25 g (0.14 mol) of potassium sulfate were reacted and the reaction product was treated in the same manner as in Example 1 to obtain 41.5 g of 4,4'-dihydroxydiphenyl. Yield: 89%.

EXAMPLE 5

111 g (0.25 mol) of 4,4'-diphenyldisulfonic acid (70.6% purity, 11.6% sulfuric acid content) and 139 g (2.38 mol) of potassium hydroxide were reacted and the reaction product was treated in the same manner as in Example 1 to obtain 40 g of 4,4'-dihydroxydiphenyl. Yield: 86%.

EXAMPLE 6

98 g (0.25 mol) of dipotassium salt of DPDS, 132 g (2.25 mol) of potassium hydroxide and 33 g (0.18 mol) of potassium sulfate were reacted under the same conditions as in Example 1. After completion of the reaction, water was added to the resulting reaction mixture to dilute the same to a potassium hydroxide concentration [(potassium hydroxide)/(potassium hydroxide+water)] of 21%. The mixture was heated to 100° C. to obtain a solution, which was cooled to room temperature and 0.23 mol of dipotassium salt of DHDP (A) thus precipitated was taken out.

The filtrate was concentrated to a potassium hydroxide concentration of 50%. 0.43 mol of potassium sulfite thus precipitated was filtered out. 1.0 mol of potassium hydroxide in the form of its aqueous solution was recovered.

The above-mentioned dipotassium salt of DHDP (A) was dissolved in water and an insoluble matter was removed. Dilute sulfuric acid was added to the solution to precipitate crystals. After the filtration, washing and drying, 42 g of DHDP was obtained. The product had a purity of 98% and ash content of 1050 ppm.

A 12-fold amount of n-butanol and 15 g of active carbon were added to DHDP and heated to 90° C. to obtain a solution. An insoluble matter and active carbon were removed. Then, n-butanol was recovered to obtain DHDP having a purity of 99.9% and ash content of 80 ppm. Yield: 88% (0.22 mol).

EXAMPLE 7

701 g of potassium hydroxide (12 mol, 96% purity) was charged in a 1 l reaction vessel provided with a stirrer and thermometer. The temperature was elevated to 320° C. to fuse potassium hydroxide.

1 mol of dipotassium 4,4'-diphenyldisulfonate (84% purity, 16% $K_2SO_4$) were added thereto over 2 h and the mixture was maintained at that temperature for additional 2 h to complete the reaction. Water was added to the resulting reaction mixture to dilute the same to a potassium hydroxide concentration [(potassium hydroxide)/(potassium hydroxide+water)] of 22%. The mixture was heated to 100° C. to obtain a solution, which was cooled to room temperature and 0.94 mol of dipotassium salt of DHDP (A) thus precipitated was filtered out.

The filtrate was concentrated to a potassium hydroxide concentration of 50%. Crystals of potassium sulfite thus formed were filtered out to obtain 1.7 mol (theoretical amount: 2.0 mol) of potassium sulfite. 7.0 mol (theoretical amount: 8.0 mol) of potassium hydroxide in the form of its aqueous solution was recovered. The aqueous potassium hydroxide solution thus recovered could be used repeatedly more than 10 times after the treatment with active carbon.

Dipotassium salt of DHDP (A) was dissolved in water and an insoluble matter was removed. The solution was treated with 50% sulfuric acid, filtered and washed with water to obtain pure-white DHDP having a purity of 99.5% and ash content of 250 ppm. Yield: 92% (0.92 mol).

DHDP obtained as above was dried and a 12-fold amount of n-butanol and a small amount of active carbon were added to it and heated to 90° C. to obtain a solution. An insoluble matter and active carbon were removed. Then, n-butanol was distilled out from the filtrate to obtain DHDP having an ash content of 70 ppm. Yield: 90% (0.90 mol).

EXAMPLES 8–19

The same procedure as in Example 1 was repeated except that the conditions were varied properly.

The results are summarized in the following table.

TABLE

| Example | Alkali fusion[1] DPDS $K_2$ (mol) | Alkali fusion[1] KOH (mol) | Control of[2] KOH conc. KOH conc. (%) | Control of[2] KOH conc. DHDP $K_2$ (mol) | KOH Conc. KOH conc. (%) | KOH Conc. $K_2SO_3$[3] (mol) | Recovered[4] KOH (mol) | Crude DHDP (mol) | Solvent | Purified DHDP (mol) | Quality Purity (%) | Quality Ash content (ppm) |
|---|---|---|---|---|---|---|---|---|---|---|---|---|
| 8  | 1 | 12 | 23 | 0.94 | 52 | 1.7 | 7.0 | 0.93 | n-Butanol  | 0.92 | 99.3 | 70 |
| 9  | 1 | 12 | 25 | 0.95 | 60 | 1.6 | 6.3 | 0.93 | ″          | 0.91 | 99.7 | 60 |
| 10 | 1 | 12 | 22 | 0.91 | 53 | 1.7 | 7.1 | 0.90 | n-Propanol | 0.88 | 99.3 | 70 |
| 11 | 1 | 12 | 23 | 0.93 | 51 | 1.7 | 7.0 | 0.91 | Iso-propanol | 0.88 | 99.1 | 60 |
| 12 | 1 | 12 | 22 | 0.93 | 50 | 1.7 | 6.9 | 0.90 | Octanol    | 0.87 | 99.0 | 70 |
| 13 | 1 | 12 | 21 | 0.92 | 50 | 1.7 | 7.2 | 0.89 | ″          | 0.87 | 99.4 | 80 |
| 14 | 1 | 12 | 24 | 0.95 | 50 | 1.7 | 7.2 | 0.94 | n-Butanol  | 0.91 | 99.3 | 70 |

TABLE-continued

| | Alkali fusion[1] | | Control of[2] KOH conc. | | KOH Conc. | | | | | Quality | |
|---|---|---|---|---|---|---|---|---|---|---|---|
| Example | DPDS K2 (mol) | KOH (mol) | KOH conc. (%) | DHDP K2 (mol) | KOH conc. (%) | K2SO3[3] (mol) | Recovered[4] KOH (mol) | Crude DHDP (mol) | Solvent | Purified DHDP (mol) | Purity (%) | Ash content (ppm) |
| 15 | 1 | 12 | 25 | 0.95 | 49 | 1.7 | 7.3 | 0.92 | Ethyl-acetate | 0.90 | 99.1 | 70 |
| 16 | 1 | 12 | 25 | 0.96 | 43 | 1.8 | 7.3 | 0.95 | Ethyl-acetate | 0.92 | 99.0 | 70 |
| 17 | 1 | 12 | 22 | 0.93 | 45 | 1.7 | 7.2 | 0.91 | n-Propanol | 0.88 | 99.3 | 70 |
| 18 | 1 | 12 | 22 | 0.94 | 50 | 1.7 | 6.8 | 0.92 | " | 0.90 | 99.2 | 80 |
| 19 | 1 | 12 | 22 | 0.94 | 52 | 1.7 | 6.8 | 0.91 | n-Butanol | 0.88 | 99.1 | 80 |

Notes:
[1]DPDSK2: Dipotassium 4,4'-diphenyldisulfonate
[2]DHDPK2: Dipotassium salt of 4,4'-dihydroxydiphenyl
[3]Theoretical amount: 2.0 mol
[4]Theoretical amount: 8.0 mol.

What is claimed is:

1. A process for producing 4,4'-dihydroxydiphenyl by fusing 4,4'-diphenyldisulfonic acid or a salt thereof in the presence of potassium hydroxide, which comprises, subjecting at least one of 4,4'-diphenyldisulfonic acid and potassium 4,4'-diphenyldisulfonate to alkali fusion at a temperature of 280° to 330° C. with 4 to 10 mol of otassium hydroxide and 0.1 to 2 mol of potassium sulfate per mol of the at least one 4,4'-diphenyldisulfonic acid and potassium 4,4'-diphenyldisulfonate, dissolving the reaction mixture in water, and adding an acid to the solution to crystallize 4,4'-dihydroxydiphenyl.

2. A process for producing 4,4'-dihydroxydiphenyl according to claim 1, wherein potassium sulfate is used in an amount of 0.2-1.0 mol.

3. A process for producing 4,4'-dihydroxydiphenyl according to claim 1, wherein the reaction mixture is cooled after the alkali fusion and the mixture is dissolved in water, an insoluble matter is filtered out, and then the filtrate is neutralized with an acid to form crystals of 4,4'-dihydroxydiphenyl and the crystals are filtered out.

4. A process for producing 4,4'-dihydroxydiphenyl by fusing 4,4'-diphenyldisulfonic acid or a salt thereof in the presence of potassium hydroxide, which comprises, subjecting 4,4'-diphenyldisulfonic acid or a salt thereof to the alkali fusion at a temperature of 280° to 330° C. with potassium hydroxide and 0.1 to 2.0 mol of potassium sulfate per mol of the 4,4'-diphenyldisulfonic acid or salt thereof, adding water to the reaction mixture to control the potassium hydroxide concentration to 20-25% and precipitate 4,4'-dihydroxydiphenyl in the form of crystals (A) of its dipotassium salt, filtering the crystals (A) out, concentrating the filtrate to a potassium hydroxide concentration of 40-60%, and separating the thus-formed crystals of potassium sulfite out of the aqueous potassium hydroxide solution, and dissolving crystals (A) in water and adding an acid to the resulting solution to crystallize 4,4'-dihydroxydiphenyl.

5. A process for producing 4,4'-dihydroxydiphenyl according to claim 4, wherein dipotassium salt of 4,4'-dihydroxydiphenyl is dissolved in water, the resulting solution is neutralized with an acid and 4,4'-dihydroxydiphenyl thus crystallized is separated.

6. A process for producing 4,4'-dihydroxydiphenyl according to claim 4, wherein the aqueous potassium hydroxide solution from which the crystals of potassium sulfite have been removed is used for the alkali fusion of 4,4'-diphenyldisulfonic acid or a salt thereof.

7. A process for producing 4,4'-dihydroxydiphenyl by fusing 4,4'-diphenyldisulfonic acid or a salt thereof in the presence of potassium hydroxide, which comprises, subjecting 4,4'-diphenyldisulfonic acid or a salt thereof to the alkali fusion at a temperature of 280° to 330° C. with potassium hydroxide and 0.1 to 2.0 mol of potassium sulfate per mol of the 4,4'-diphenyldisulfonic acid or salt thereof, adding water to the reaction mixture to control the potassium hydroxide concentration to 20-25% and precipiate 4,4'-dihydroxydiphenyl in the form of crystals (A) of its dipotassium salt, filtering the crystals (A) out to leave a filtrate (b), dissolving the crystals (A) in water, adding an acid thereto, and separating the thus-formed crude crystals of 4,4'-dihydroxidiphenyl, drying and then dissolving the crude crystals in at least one solvent selected from the group consisting of aliphatic alcohols having 3-8 carbon atoms and aliphatic carboxylic acid esters having 3-8 carbon atoms in total in the presence of active carbon, filtering the active carbon out, and removing the solvent to obtain 4,4'-dihydroxydiphenyl, and concentrating the filtrate (b) to a potassium hydroxide concentration of 40-60%, and separating the thus-formed crystals of potassium sulfite out of the aqueous potassium hydroxide solution.

8. A process for producing 4,4'-dihydroxydiphenyl according to claim 7, wherein the aliphatic alcohol or aliphatic carboxylic acid ester is n-butanol, n-propanol, isopropanol, octanol, ethyl acetate or a mixture of them.

9. A process for producing 4,4'-dihydroxydiphenyl according to claim 7, wherein the aqueous potassium hydroxide solution from which the crystals of potassium sulfite have been filtered out is used for the alkali fusion of 4,4'-diphenyldisulfonic acid or a salt thereof.

10. A process for producing 4,4'-dihydroxydiphenyl by fusing 4,4'-diphenyldisulfonic acid or a salt thereof in the presence of potassium hydroxide, which comprises, subjecting 4,4'-diphenyldisulfonic acid or a salt thereof to the alkali fusion at a temperature of 280° to 330° C. by using a 4-10 mol of potassium hydroxide and 0.1-2 mol of potassium sulfate per mol of the 4,4'-diphenyldisulfonic acid or salt thereof, adding water to the reaction mixture to control the potassium hydroxide concentration to 20-25% and precipitate 4,4'-dihydroxydiphenyl in the form of crystals (A) of its dipotassium salt, filtering the crystals (A) out to leave a filtrate, concentrating the filtrate to a potassium hydroxide concentration of 40–60%, and separating the thus-formed crystals of potassium sulfite out of the aqueous potassium hydroxide solution, and dissolving the crystals (A) in water and adding an acid to the resulting solution to crystallize 4,4'-dihydroxydiphenyl.

11. A process for producing 4,4'-dihydroxydiphenyl according to claim 10, wherein dipotassium salt of 4,4'-dihydroxydiphenyl is dissolved in water, the resulting solution is neutralized with an acid and 4,4'-dihydroxydiphenyl thus precipitated is separated.

12. A process for producing 4,4'-dihydroxydiphenyl according to claim 10, wherein the aqueous solution of potassium hydroxide from which the crystals of potassium sulfite have been separated is used for the alkali fusion of 4,4'-diphenyldisulfonic acid or a salt thereof.

13. A process for producing 4,4'-dihydroxydiphenyl by fusion 4,4'-diphenyldisulfonic acid or a salt thereof in the presence of potassium hydroxide, which comprises, subjecting 4,4'-diphenyldisulfonic acid or a salt thereof to the alkali fusion at a temperature of 280° to 330° C. by using 4–10 mol of potassium hydroxide and 0.1–2 mol of potassium sulfate per mol potassium sulfate per mol of the 4,4'-diphenyldisulfonic acid or salt thereof, adding water to the reaction mixture to control the potassium hydroxide concentration to 20–25% and to precipitate 4,4'-dihydroxydiphenyl in the form of crystals (A) of its dipotassium salt, filtering the crystals (A) out to leave a filtrate (B), dissolving the crystals (A) in water and adding an acid thereto, and separating the thus-formed crude crystals of 4,4'-dihydroxydiphenyl drying and then dissolving the crude crystals in at least one solvent selected from the group consisting of aliphatic alcohols having 3–8 carbon atoms and aliphatic carboyxlic acid esters having 3–8 carbon atoms in total in the presence of active carbon, filtering the active carbon out, and removing the solvent to obtain 4,4'-dihydroxydiphenyl, and concentrating the filtrate (B) to a potassium hydroxide concentration to 40–60% and separating the thus-formed crystals of potassium sulfite out of the aqueous potassium hydroxide solution.

14. A process for producing 4,4'-dihydroxydiphenyl according to claim 13, wherein 0.2–1.0 mol of potassium sulfate is used.

15. A process for producing 4,4'-dihydroxydiphenyl according to claim 13, wherein the aqueous potassium hydroxide solution from which the crystals of potassium sulfite have been separated is used for the alkali fusion of 4,4'-diphenyldisulfonic acid or a salt thereof.

16. A process for producing 4,4'-dihydroxydiphenyl according to claim 13, wherein the aliphatic alcohol or aliphatic carboxylic acid ester is n-butanol, n-propanol, isopropanol, octanol, ethyl acetate or a mixture of them.

* * * * *